(12) United States Patent
Farnsworth (10) Patent No.: US 7,186,972 B2
(45) Date of Patent: Mar. 6, 2007

(54) TIME OF FLIGHT MASS ANALYZER HAVING IMPROVED MASS RESOLUTION AND METHOD OF OPERATING SAME

(75) Inventor: Vincent R. Farnsworth, Agoura, CA (US)

(73) Assignee: Beckman Coulter, Inc., Fullerton, CA (US)

( * ) Notice: Subject to any disclaimer, the term of this patent is extended or adjusted under 35 U.S.C. 154(b) by 146 days.

(21) Appl. No.: 10/692,301

(22) Filed: Oct. 23, 2003

(65) Prior Publication Data

US 2005/0087684 A1 Apr. 28, 2005

(51) Int. Cl.
*H01J 49/40* (2006.01)
*H01J 49/28* (2006.01)
*B01D 59/44* (2006.01)

(52) U.S. Cl. .................. 250/287; 250/294; 250/281
(58) Field of Classification Search ............... 250/287, 250/290, 291
See application file for complete search history.

(56) References Cited

U.S. PATENT DOCUMENTS

| | | | |
|---|---|---|---|
| 3,136,888 A | 6/1964 | Andras et al. | |
| 3,239,662 A | 3/1966 | Noller | |
| 3,555,271 A | 1/1971 | Brubaker et al. | |
| 3,634,683 A | * 1/1972 | Bakker | 250/282 |
| 3,925,663 A | 12/1975 | Hiller et al. | |
| 3,970,849 A | 7/1976 | Brongersma et al. | |
| 4,059,761 A | 11/1977 | Dawson | |
| 4,081,677 A | 3/1978 | Dawson | |
| 4,126,804 A | 11/1978 | Asam et al. | |
| 4,208,582 A | 6/1980 | Arnush et al. | |
| 4,221,964 A | 9/1980 | Schlereth et al. | |

(Continued)

FOREIGN PATENT DOCUMENTS

GB 1 302 194 1/1973

(Continued)

*Primary Examiner*—Nikita Wells
(74) *Attorney, Agent, or Firm*—Maginot, Moore & Beck (57) ABSTRACT

A time-of-flight mass analyzer having improved mass resolution without mandating a corresponding increase in instrument size is disclosed. The analyzer includes an ionizer that generates the ions that are to be analyzed. These ions are introduced to an ion flight path, at least a portion of which is aligned with a linear axis. The portion of the ion path that is aligned with the linear axis includes a region having a substantially static electric field with non-linear equipotential field lines that circumvent the linear axis. Ions either enter the substantially static electric field with a velocity component that is directed along the linear axis or have such a velocity component imparted to them once they have been trapped in the substantially static electric field. As a result of the combined effects of the linear velocity component and the non-linear field, the ions make multiple circumnavigating trips about the linear axis as they concurrently travel in the direction of the linear axis. Consequently, the ions travel along a significantly longer flight path when compared to a flight path in which the ions solely travel linearly along the axis. In one embodiment, the concurrent motions of the ions in the direction of the linear axis and along the equipotential field lines about the linear axis define a substantially helical ion trajectory. This provides a larger distance along which ions having close, but different, m/z may be separated in time thereby providing an instrument having higher resolution.

26 Claims, 8 Drawing Sheets

U.S. PATENT DOCUMENTS

| | | | |
|---|---|---|---|
| 4,490,610 A * | 12/1984 | Ulbricht, Jr. | 250/287 |
| 4,774,408 A | 9/1988 | Gohlke | |
| 4,945,236 A | 7/1990 | Mogami et al. | |
| 4,982,088 A | 1/1991 | Weitekamp et al. | |
| 5,495,108 A | 2/1996 | Apffel, Jr. et al. | |
| 5,726,448 A | 3/1998 | Smith et al. | |
| 5,861,623 A * | 1/1999 | Park | 250/287 |
| 5,886,346 A * | 3/1999 | Makarov | 250/291 |
| 6,410,914 B1 | 6/2002 | Park et al. | |
| 6,791,077 B1 * | 9/2004 | Farnsworth | 250/285 |
| 6,791,079 B2 * | 9/2004 | Glukhoy | 250/287 |
| 6,794,647 B2 * | 9/2004 | Farnsworth et al. | 250/293 |
| 6,828,553 B2 * | 12/2004 | Weiss | 250/287 |

FOREIGN PATENT DOCUMENTS

| | | |
|---|---|---|
| WO | WO 95/00237 | 1/1995 |
| WO | WO 95/23018 | 8/1995 |
| WO | WO 02/01599 | 1/2002 |

* cited by examiner

TIME OF FLIGHT MASS ANALYZER HAVING IMPROVED MASS RESOLUTION AND METHOD OF OPERATING SAME

FIELD OF THE INVENTION

The present invention is generally directed to mass analyzers. More particularly, the present invention is directed to a time-of-flight mass analyzer having improved mass resolution.

BACKGROUND OF THE INVENTION

The characteristics of mass spectrometry have raised it to an outstanding position among the various analysis methods. It has excellent sensitivity and detection limits and may be used in a wide variety of applications, e.g. atomic physics, reaction physics, reaction kinetics, geochronology, biomedicine, ion-molecule reactions, and determination of thermodynamic parameters ($\Delta G°_f$, $K_a$, etc.). Mass spectrometry technology has thus begun to progress very rapidly as its uses have become more widely recognized. This has led to the development of entirely new instruments and applications.

Different types of mass analyzers have been found suitable for different needs, each type having its own unique benefits and deficits. One type of mass analyzer that has been found useful in a wide range of existing and newly developed applications is the time-of-flight mass analyzer. Time-of-flight (TOF) mass spectrometers are routinely used for the analysis of high-molecular weight compounds in a variety of fields of study, including DNA and protein analysis. Although time-of-flight instruments are usually large and expensive due to the nature of the technique, the analysis times are typically short because there is no need to scan through an m/z range to get results. The analytes are typically analyzed concurrently and are distinguished by their velocities, which determine the flight time to a detector.

Figure 1:
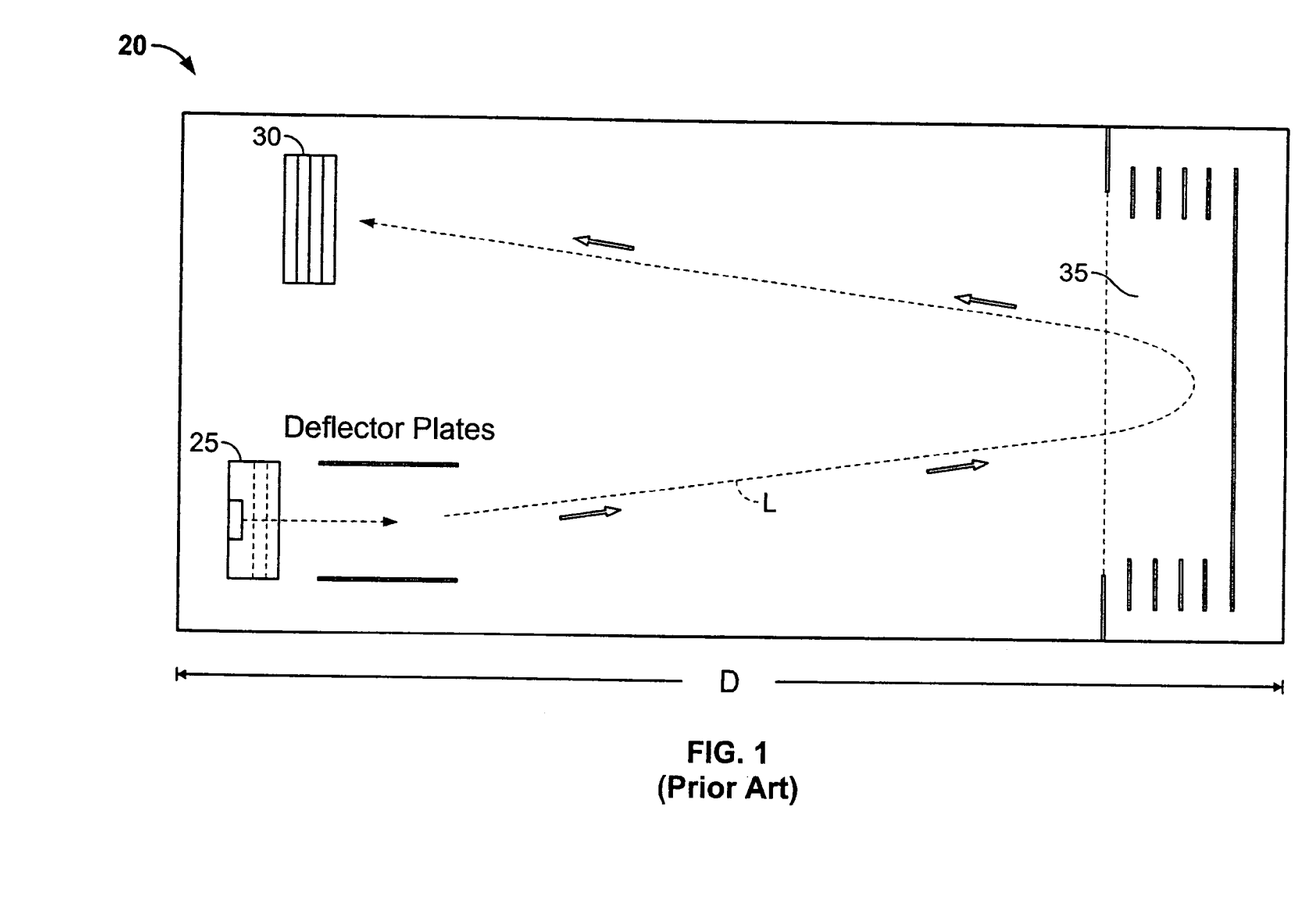
FIG. 1 illustrates a time-of-flight mass analyzer constructed in accordance with the teachings of the prior art.

FIG. 1 illustrates the basic components of a time-of-flight mass spectrometer 20. In operation the time-of-flight mass spectrometer 20 works by measuring the time it takes an ion to travel a distance L along an ion flight path. Typically, this distance corresponds to the length of the flight path traveled by the ion from a position proximate an ion source 25 to an ion detector 30. All ions are accelerated in the same electric field so initial velocities are directly proportional to their mass/charge ratio (m/z). Ions with a low m/z have higher velocities than those with higher m/z and reach the detector 30 sooner. The equation describing this relationship is the simple time-distance equation:

$$tof = L/v_a = L/[2zQV/m]^{1/2} \quad \text{(Equation 1)}$$

where tof is flight time, L is measured distance through which the ions travel in the ion flight path, $v_a$ is the velocity of the ions after acceleration, m is mass, z is the number of charges on the molecule, Q is the magnitude of the electric charge and V is the accelerating potential.

Notably, time-of-flight mass spectrometers are quite large since the ions must have a long flight path if the measured time-of-flight values are to be meaningful. Path lengths on the order of one to two meters are necessary to insure that ions of slightly different m/z are resolved. The flight time under typical conditions for ions in the 1000 m/z range is about 70 microseconds and flight time differences at the highest resolution are on the order of nanoseconds.

Some of the factors affecting flight time include the initial ionization and acceleration conditions as well as the m/z of the ion. If large amounts of energy are used or if large accelerations are applied, the flight times will be short and differences in the flight times between ions of similar m/z will be slight. However, despite the negative effect of imparting such high levels of energy to the ions, it is often necessary to give the ions that are to be analyzed high acceleration potentials (up to ~30 kV) so that the differences in the initial conditions (i.e., kinetic energy spread) of identical ions are minimized. With reference again to FIG. 1, some time-of-flight mass spectrometers may be equipped with a reflectron 35 to compensate for such variations in the initial kinetic energy of ions having the same m/z.

As the uses of time-of-flight mass spectrometry have increased, so too have the requirements for increased mass sensitivity and resolution that are imposed upon these instruments. Because the flight time of the ions along the flight path is short, especially with reasonably sized instruments, compounds of similar m/z are difficult to distinguish and, as such, relatively low resolutions on the order of only several hundreds are typical of these instruments. The resolution may be increased by lengthening the flight path L so that molecules of similar size traveling at slightly different velocities may be separated. Lengthening of the flight path L, however, has traditionally been accomplished by increasing dimension D of the analyzer 20 thereby leading to substantially larger instruments. Thus, development trends with respect to time-of-flight mass spectrometers have gone in the direction of large, increasingly complex designs requiring highly specialized components and tight manufacturing tolerances.

SUMMARY OF THE INVENTION

A time-of-flight mass analyzer having improved mass resolution without mandating a corresponding increase in instrument size is disclosed. The analyzer includes an ionizer that generates the ions that are to be analyzed. These ions are introduced to an ion flight path, at least a portion of which is aligned with a linear axis. The portion of the ion path that is aligned with the linear axis includes a region having a substantially static electric field with non-linear equipotential field lines that circumvent the linear axis. Ions either enter the substantially static electric field with a velocity component that is directed along the linear axis or have such a velocity component imparted to them once they have been trapped in the substantially static electric field. As a result of the combined effects of the linear velocity component and the non-linear field, the ions make multiple circumnavigating trips about the linear axis as they concurrently travel in the direction of the linear axis. Consequently, the ions travel along a significantly longer flight path when compared to a flight path in which the ions solely travel linearly along the axis. In one embodiment, the concurrent motion of the ions in the direction of the linear axis and along the equipotential field lines about the linear axis defines a substantially helical ion trajectory. This provides a larger distance along which ions having close, but different, m/z may be separated in time thereby providing an instrument having higher resolution.

In accordance with one embodiment of the analyzer, the linear portion of the ion flight path includes a flight tube having an inlet portion adapted to direct ions received therethrough to a region that is substantially free of electric fields, and an ion deflection portion having the substantially static electric field described above. The ion deflection portion is adapted to direct ions received from the inlet portion along a generally helical ion flight path defined, at least in part, by the equipotential field lines of the substantially static electric field.

The flight tube may comprise a first electrode, a second electrode and a third electrode having a unique interrelationship. The first electrode includes a generally cylindrical electrode surface that faces an interior portion thereof and an ion inlet disposed through its side. The second electrode includes a generally cylindrical electrode surface that faces an exterior portion thereof. Preferably, the second electrode is concentrically disposed with the first electrode. Further, the second electrode includes an arcuate opening along its electrode surface. The arcuate opening is located at least in a region proximate the ion inlet. Finally, the third electrode includes an arcuate electrode surface that faces an exterior portion thereof. The third electrode is disposed in the arcuate opening of the second cylindrical electrode.

At least one power supply is connected to the first, second and third electrodes. The power supply is operable to generate a first generally static electric field between the first and second electrodes, and is alternately operable between at least a first state in which the region between the first and third electrodes proximate the ion inlet is generally field free, and a second state in which a second generally static electric field is generated in the region between the first electrode and the second and third electrodes. Preferably, the first and second generally static electric fields have substantially the same magnitudes.

DESCRIPTION OF A PREFERRED EMBODIMENT OF THE INVENTION

Figure 2:
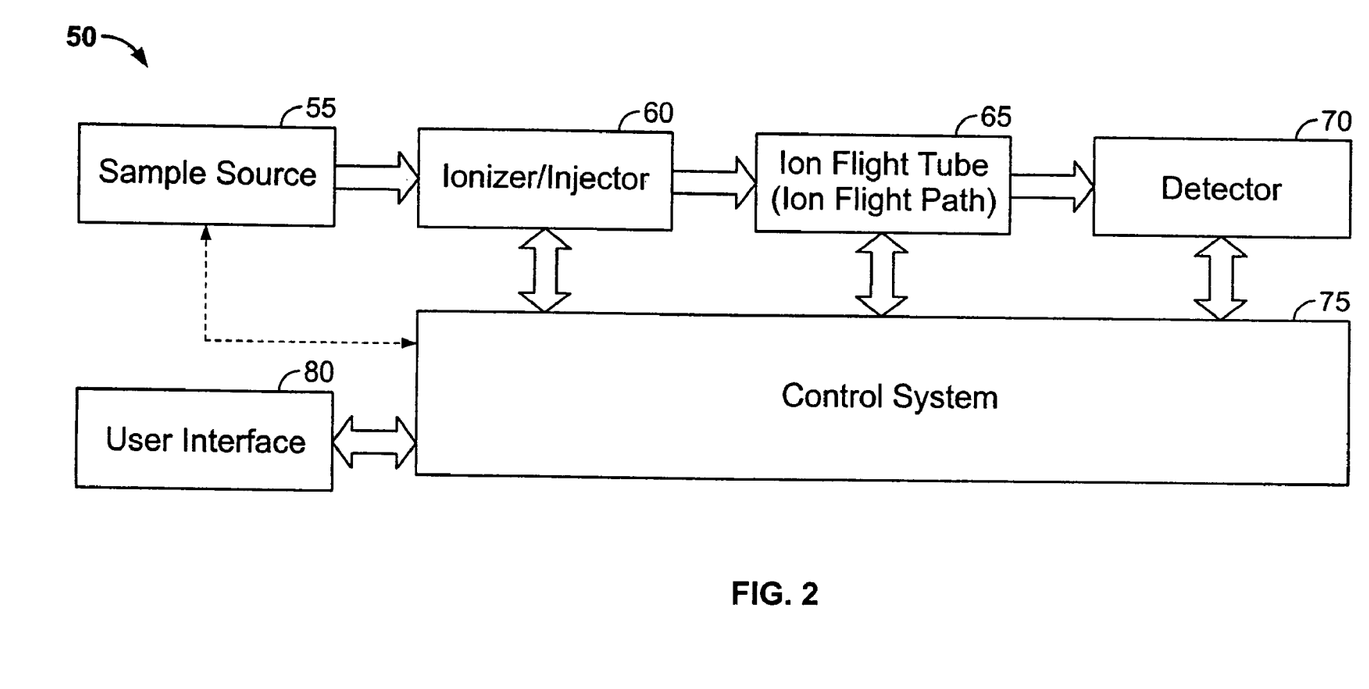
FIG. 2 is a schematic block diagram of one embodiment of a time-of-flight mass spectrometer constructed in accordance with one embodiment of the present invention.

The basic components of a time-of-flight mass analyzer constructed in accordance with one embodiment of the invention are shown in FIG. 2 in block diagram form. As illustrated, the analyzer 50 includes a sample source unit 55, an ionizer/ion injector 60, an ion flight path that includes ion flight tube 65, and an ion detector 70. Although the term "tube" has been used in connection with schematic block 65, the use of the term has been undertaken for the sake of simplicity and is not meant to constrain the corresponding structure to a particular shape. Rather, the term is intended to encompass all of the various element shapes that can be used to constrain ions to a flight path of the type set forth below.

The components of the mass analyzer 50 may be automated by one or more programmable control systems 75. To this end, control system 75 may be used to execute one or more of the following automation tasks:

a) control of the ionization and ion injection parameters of one or more of the components of the ionizer/ion injector 60 (i.e., ion beam focusing, ion beam entrance angle into the ion flight tube 65, ion injection timing, ionization energy, ion exit velocity, etc.);

b) control of the electric field parameters within the ion flight path including ion flight tube 65;

c) measurement of the time-of-flight of ions through the ion flight tube 60; and d) analysis of the data received from the mass analyzer 50 for presentation to a user and/or for subsequent data processing and/or analysis.

The parameters used to execute one or more of the foregoing automation tasks may be entered into the control system 75 by a human operator through, for example, user interface 80. Additionally, user interface 80 may be used to display information to the human operator for system monitoring purposes or the like. As such, user interface 80 may include a keyboard, display, switches, lamps, touch display, printers or any combination of these items.

With reference to FIG. 2, the material that is to be analyzed is provided to analyzer 50 through the sample source unit 55. Sample source unit 55 may include a single sample outlet or multiple sample outlets (a single sample outlet is shown in the illustrated embodiment). Further, the sample source unit 55 can be configured to provide a single material type or multiple successive material types.

The sample material from the sample source unit 55 is provided to the input of the ionizer/ion injector 60. Sample source unit 55 can introduce the sample material (which includes the analyte) to the ionizer/ion injector 60 in several ways, the most common being with a direct insertion probe, or by infusion through a capillary column. The ionizer/ion injector 60 may therefore be adapted to interface directly with whatever form the sample takes at the output of the sample source unit 55. For example, the ionizer/ion injector 60 can be adapted to interface directly with the output of gas chromatography equipment, liquid chromatography equipment, and/or capillary electrophoresis equipment. It will be recognized that any treatment of a sample material prior to the point at which sample source unit 55 provides it to the ionizer/ion injector 60 is dependent on the particular analysis requirements.

Upon receiving the sample from the sample source 55, the ionizer/ion injector 60 operates to ionize the molecules of the analyte included in the received sample and to inject the ionized analyte molecules, either directly or indirectly, into the ion flight tube 65. Although pulsed ionization techniques providing short, precisely defined ionization times and a small ionization region are preferable, the ionization and injection can be accomplished using any of a number of techniques. For example, one method that allows for the ionization and transfer of the sample material from a condensed phase to the gas phase is known as Matrix-Assisted Laser Desorption/Ionization (MALDI). Another technique is known as Fast Atom/Ion Bombardment (FAB), which uses a high-energy beam of Xe atoms, $Cs^+$ ions, or massive glycerol-$NH_4$ clusters to sputter the sample and matrix received from the sample source unit 55. The matrix is typically a non-volatile solvent in which the sample is dissolved. Although the ionizer/ion injector 60 is represented by a single block unit in the schematic of FIG. 2, it will be recognized that these processes can be executed by a single, integrated unit or in two or more separate units.

Figure 3:
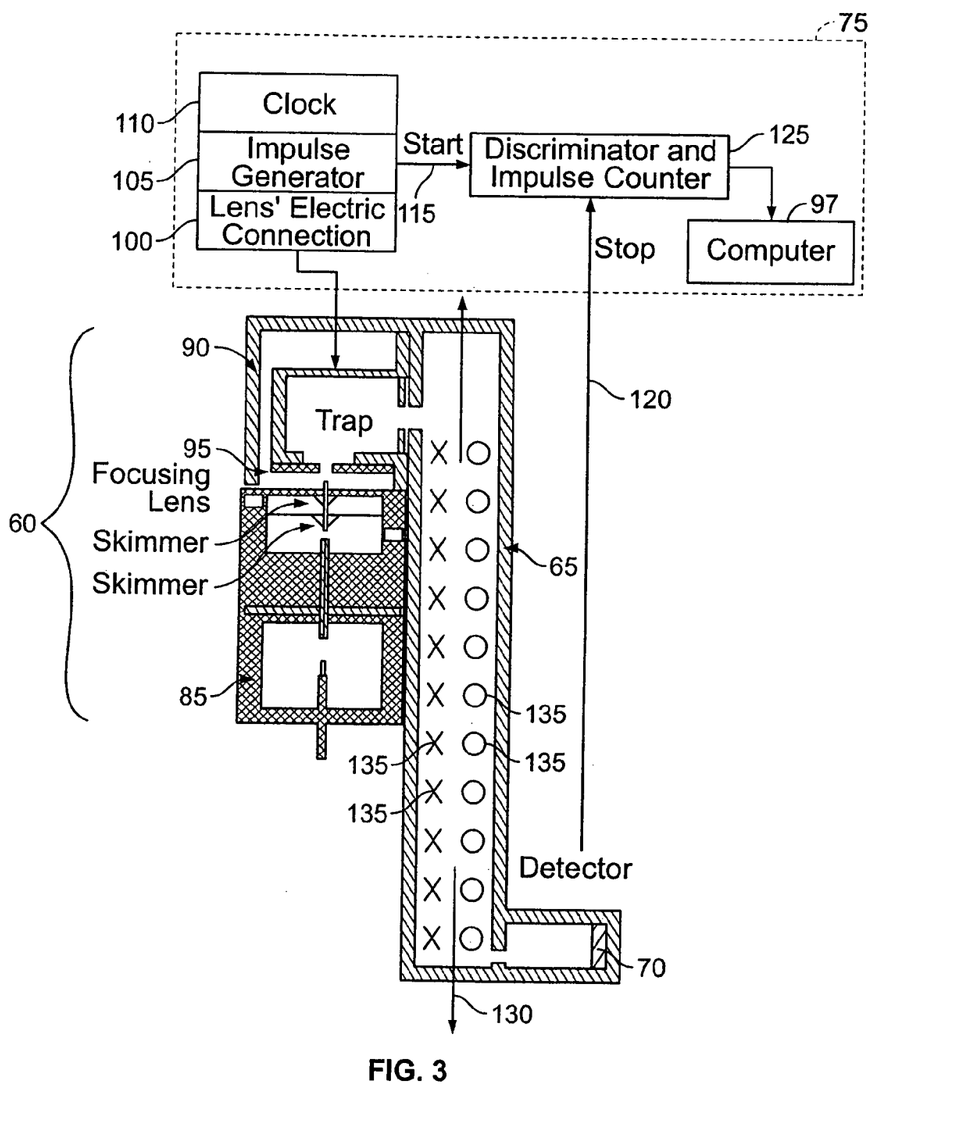
FIG. 3 is a schematic block diagram of one embodiment of several of the components that may be used in the spectrometer shown in FIG. 2.

A further technique that may be implemented by the ionizer/ion injector 60 is electrospray ionization. Since this technique is typically associated with the continuous generation of ions, however, it should be modified to provide discrete ion packets into the ion flight tube 65. One manner of doing this is shown in FIG. 3. As illustrated, ions from an electrospray generator 85 are carried to an ion trapping device 90 by low-potential lenses 95 and are stored there by a decelerating field. They are then ejected from the trapping device 90 and passed into the ion flight tube 65. For example, this may occur by applying 1 microsecond pulses that are repeated at a frequency as high as 1 kilohertz to an electrode disposed at the outlet of the trap 90.

The inlet to the ion flight tube 65 may be generally perpendicular with or at a slight angle to the direction of the ion beam exiting the trap 90. This orientation helps reduce the dispersion of the kinetic energy in the direction of the flight tube inlet. As will be set forth in the further detail below, the ion flight tube 65 itself may be adapted to initially allow it to function as an ion trap that facilitates a delayed extraction of the ions from the trap region toward the detector 70. This latter construction eliminates the need for a separate trap apparatus 90 and/or complements the operation of such a trap.

FIG. 3 also illustrates several other elements of the mass analyzer 50. More particularly, FIG. 3 illustrates the details of one embodiment of the control system 75. In this embodiment, all of the various system functions and components are preferably controlled by or executed within computer 97. Generally stated, the elements controlling ionizer/ion injector 60 include a lens control circuit 100, an impulse generator 105 and a clock circuit 110. The lens control circuit 100 and impulse generator 105 control the parameters associated with the injection of the ions into the ion flight tube 65. Lens control circuit 100 and impulse generator 105 may generate their electric fields in response to timing signals provided by clock 110. Additionally, a start signal 115 may be generated by the impulse generator 105 to indicate that a packet of ions has been injected into the ion flight path, which includes the ion flight tube 65. The start signal 115 is used to initiate a measurement sequence in which the time it takes for the packet of ions to travel along the ion flight path to the detector 70 is determined. Detector 70 is sensitive to ion impacts and is used to provide a corresponding stop signal 120 indicating that ions have exited the outlet end of flight tube 65. Both the start signal 115 and stop signal 120 are provided to a discriminator and impulse counter circuit 125 that assists in masking unwanted signals in favor of those signals that are truly indicative of the time-of-flight of the ions through the ion flight path.

As shown in FIG. 3, at least a portion of the ion flight path is aligned with a linear axis 130. In the illustrated embodiment, this axis extends along the length of the ion flight tube 65. Within the ion flight tube 65 there is a region that has a substantially static electric field. The substantially static electric field includes non-linear equipotential field lines that circumvent the linear axis 130. These non-linear equipotential field lines are shown generally at 135 and effectively extend into and from the two-dimensional representation of the flight tube 65 shown in FIG. 3. Ion motion about linear axis 130 is generally constrained by the static electric field along the non-linear equipotential field lines 135.

In accordance with a first manner of operating ion flight tube 65, it is assumed that the ions enter the substantially static electric field from the ionizer/ion injector 60 with a non-negligible velocity component in a direction along the linear axis 130. Generally stated, the path of the ions through the ion flight tube 65 is thus determined by the velocity component of the ions along the axis 130 and the distribution (shape and strength) of the equipotential field lines about the axis 130. These parameters are selected so that the ions proceed through the ion flight tube 65 in a direction along the linear axis 130 while concurrently being constrained by the static electric field to make multiple circumnavigating trips about axis 130 as the ions proceed from the flight tube inlet to the flight tube outlet. By making multiple circumnavigating trips about the axis 130 as they concurrently travel in a direction along the axis, the ions travel through a significantly longer flight path when compared to a flight path comprised solely of linear travel through flight tube 65.

Ion flight tube 65 may include the entire ion flight path within its boundaries or, alternatively, may merely constitute a portion of the overall ion flight path. For example, when the ion flight tube 65 of FIG. 3 includes substantially the entire ion flight path taken by the ions emitted from the ionizer/ion injector 60. Alternatively, an ion flight tube such as the one described here can be placed solely along a portion of an ion flight path such as the one shown in FIG. 1. As such, the ion flight path used to measure the time-of-flight of the ions may be longer than or shorter than the path that the ions take through the ion flight tube 65. In each instance, however, a flight tube 65 constructed in the foregoing manner substantially increases the overall length of the ion flight path without requiring a corresponding increase in the length of the flight path components. The increase in the overall length of the ion flight path gives rise to an increase in the resolution of the mass analyzer thereby allowing for the design of a higher-quality instrument in a smaller dimensioned package.

Figure 4:
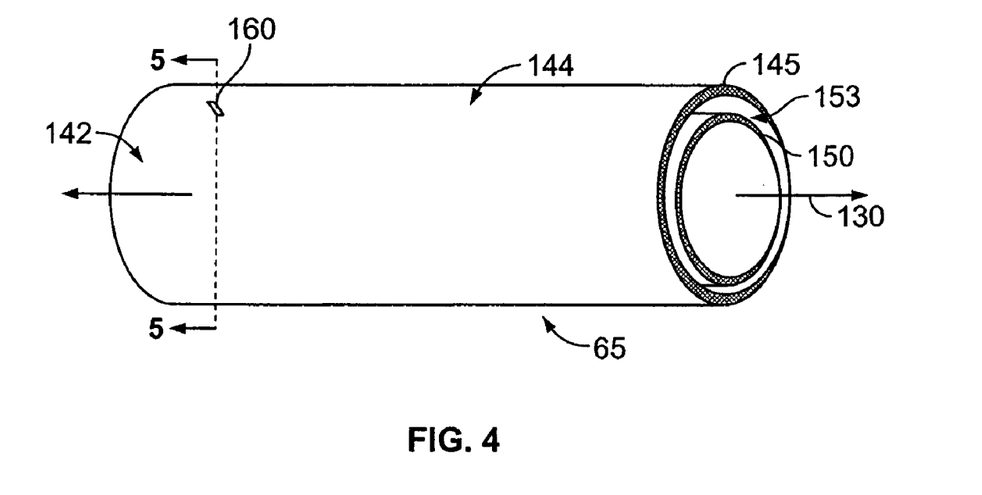
FIGS. 4 through 10 show the construction and operation of one embodiment of a flight tube suitable for use in the time-of-flight mass spectrometer shown in FIG. 2.
Figure 5:
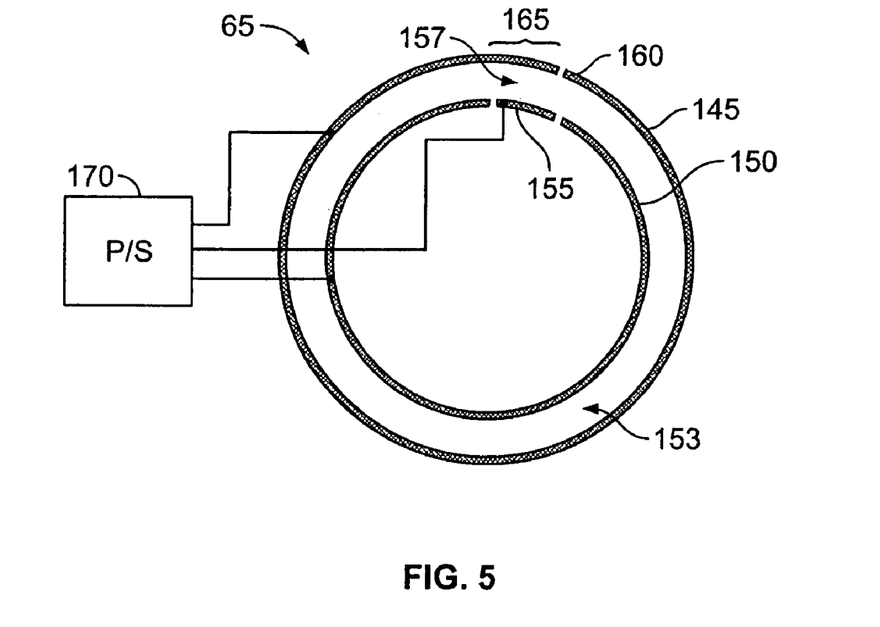

One embodiment of an ion flight tube 65 that is adapted to operate in the foregoing manner is shown in FIGS. 4 and 5. Generally stated, ion flight tube 65 includes an inlet portion 142 and an ion deflection portion 144. The ion inlet portion 142 is adapted to direct ions received therethrough to a region that is substantially free of electric fields. In contrast, the ion deflection portion 144 accepts ions from the ion inlet portion 142 and directs the ions to a region having a substantially static electric field. Within the ion deflection portion 144, the ions make the multiple circumnavigating trips about the axis 130 as they concurrently travel in a direction along the axis as described above.

In the specific embodiment of FIGS. 4 and 5, ion flight tube 65 includes a first electrode 145, a second electrode 150 and a third electrode 155. The first electrode 145 has a generally cylindrical electrode surface facing an interior portion thereof and an ion inlet 160 disposed through its side.

The second electrode 150 is concentrically disposed within the first electrode 145 and has a generally cylindrical electrode surface facing an exterior portion thereof so that an electric field may be generated in the interstitial region 153 between the first and second electrodes, 145 and 150. The second electrode 150 further includes an opening 165 through an arcuate portion of the electrode surface. Depending on the design requirements, the arcuate opening 165 may be limited solely to the region proximate the ion inlet 160 or may extend along a more substantial portion of the length of the second electrode 150.

The third electrode 155 is disposed in the arcuate opening 165 of the second electrode 150. The third electrode 155 includes an arcuate electrode surface facing an exterior portion thereof that is disposed to allow selective generation of an electric field in the interstitial region 157 between the third and first electrodes, 155 and 145, respectively. Preferably, the third electrode 155 is shaped to form a generally continuous cylindrical electrode with the second electrode 150. Such continuity facilitates selective formation of a substantially homogenous electric field in the entire interstitial region between the first electrode 145 and the combined structures of the second and third electrodes, 150 and 155.

The first, second and third electrodes may be constructed in a variety of manners. For example, they may be constructed as purely conductive members formed from a single conductive material or multiple layers of different conductive materials. They may also be constructed from a conductive material between dielectric surfaces, a conductive material disposed over a dielectric surface, etc. The principal objective of any such design should be the generation of the desired electric field within the interstitial regions. As such, for purposes of the present invention, an electrode "surface" may be exposed or covered depending on the design criterion of the mass analyzer 20.

At least one power supply circuit is connected to the first electrode 145, second electrode 150 and third electrode 155 to provide the power necessary to generate the electric fields required for operation of the flight tube 65. With respect to the specific embodiment shown here, the power supply circuit 170 is operated to generate a generally static electric field between the first and second electrodes while the ions travel in interstitial region 153 about and in the direction of linear axis 130. The power supply circuit 170 can also be switched between at least a first state in which the interstitial region 157 between the first and third electrodes is generally field free, and a second state in which a generally static electric field is generated in interstitial region 157 between the first and third electrodes.

Figure 6:
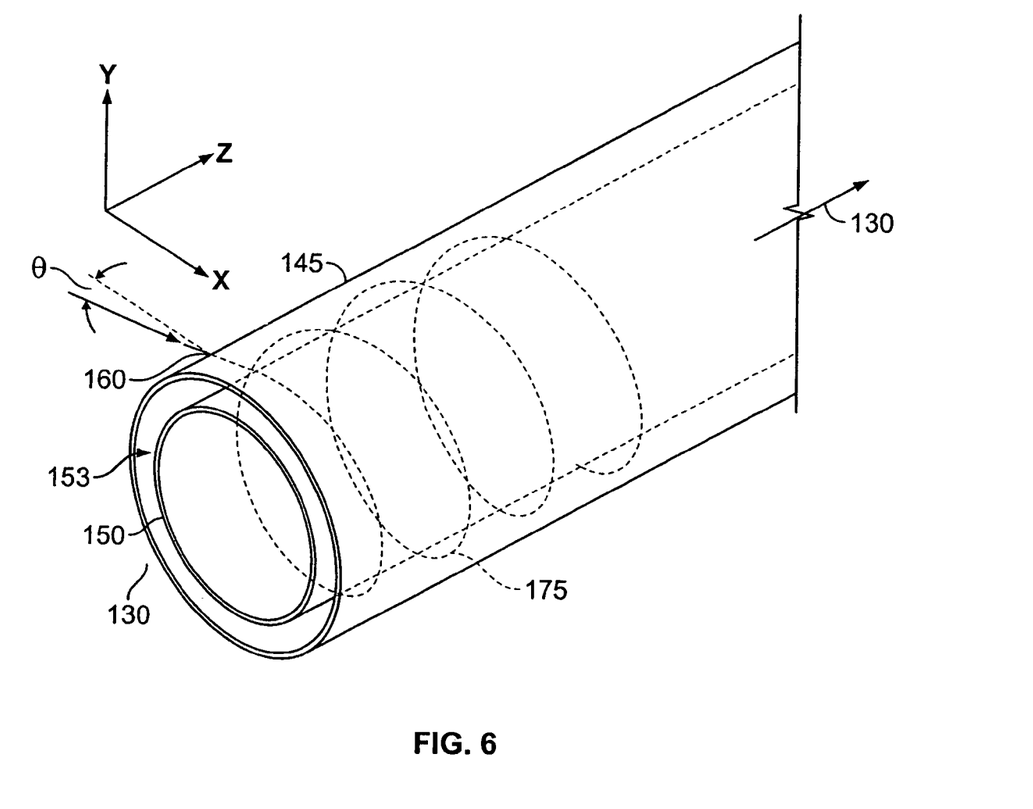
Figure 7:
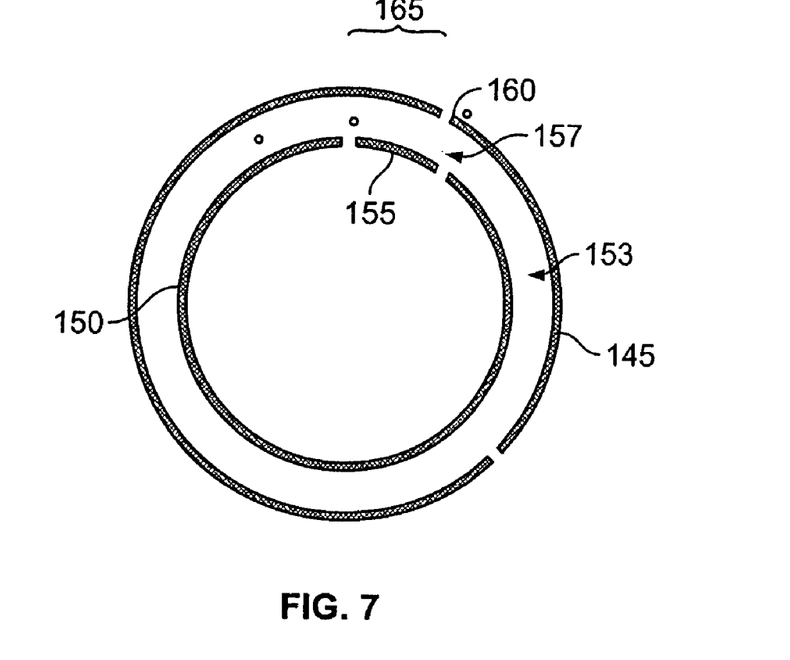

Operation of the flight tube 65 can be understood with reference to FIGS. 6–10. As shown in FIG. 6, ions are provided through the inlet 160 at a predetermined angle θ. Angle θ of this embodiment is shown as laying in the x-z the plane and is measured against the x-axis. Thus, the ions entering through inlet 160 have a velocity component in the z-direction, which coincides with the direction of the linear axis 130.

FIGS. 7 through 10 illustrate how the ions from the ionizer/ion injector 60 are inserted into the flight tube 65 and attain stable trajectories. To this end, the first electrode 145 is held at ground potential and acts as a shield so that ions from the ionizer/ion injector 60 are initially unaffected by the electric field inside the flight tube 65. A negative DC voltage is generated by power supply 170 and placed on the second electrode 150 to generate a generally static electric field throughout interstitial region 153.

Figure 8:
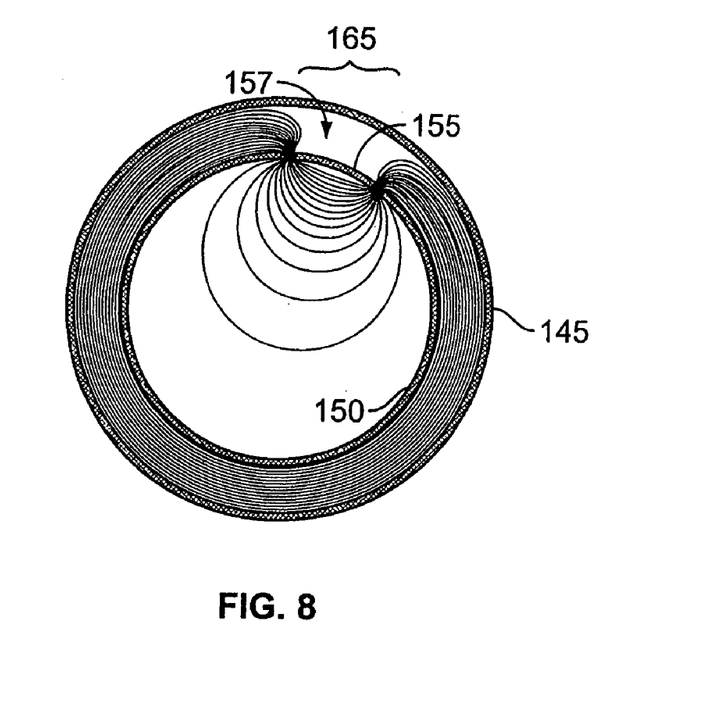

The ions must be placed into the center of the electric field of region 153 approximately halfway between the first and second electrodes, 145 and 150, or the ions will crash into the electrode walls. To direct the ions in this manner, third electrode 155 is selectively provided with power from power supply 170 to control the electric field in region 157 proximate the inlet port 160. More particularly, third electrode 155 is maintained at the same potential as first electrode 145 during initial introduction of the ions into the ion flight tube 65. Ions entering the flight tube 65 thus initially travel through a field-free zone in region 157 since there is no potential difference between the first and third electrodes, 145 and 155 at this point in time. Consequently, the ions are not deflected from their initial straight path. While in this straight path, the ions are directed to a region midway between the first and second electrodes, 145 and 150. The field-free zone that exists in region 157 as well as the equipotential field lines of the electric field generated between the first electrode 145 and second electrode 150 are illustrated in FIG. 8.

Figure 9:
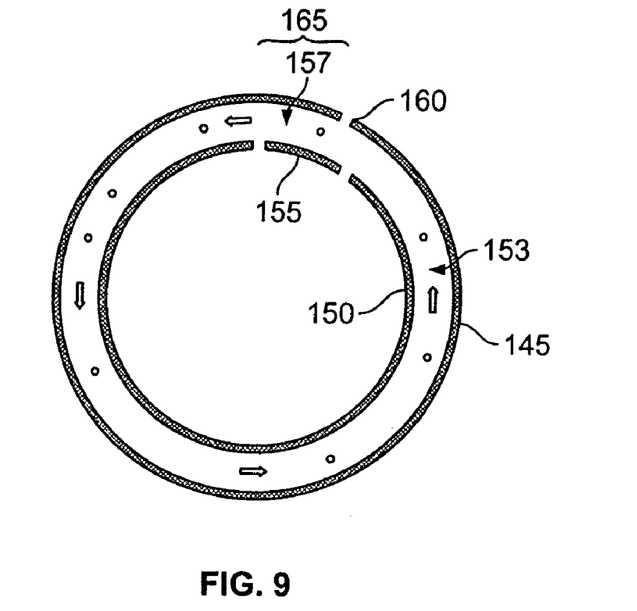
Figure 10:
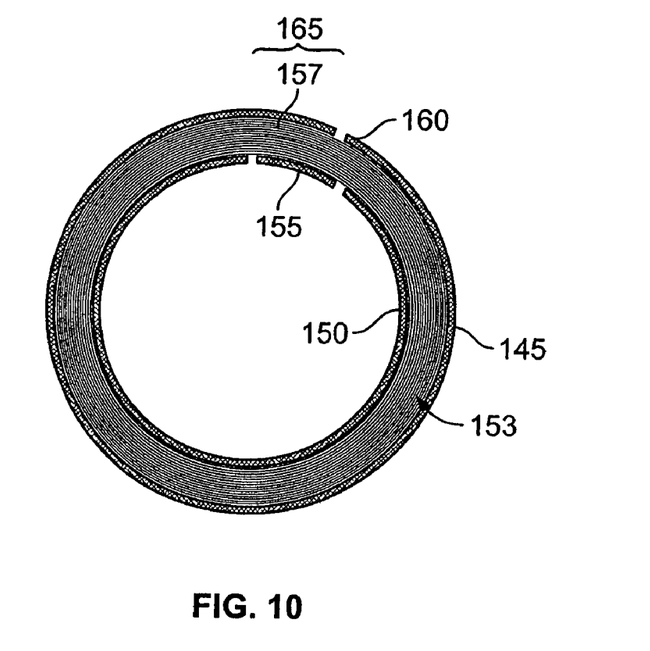

As the ions proceed further into the flight tube 65, they enter the electric field that is generated between the first and second electrodes, 145 and 150. Preferably, the ions are inserted at a negligible angle (i.e., 0°) relative to the field equipotential lines shown in FIG. 8 and are unaffected by fringe fields at their insertion point into region 157. After entry into the electric field of region 153, the ions attain a stable trajectory about and in the direction of axis 130 to thereby fly in a helical pattern, such as the flight pattern shown at 175 of FIG. 6. In order to ensure maximum stability of the ions along this helical trajectory, the power supply 170 brings the potential of the third electrode 155 to the same potential as second electrode 150 before the ions complete a full circumnavigational cycle about axis 130 and again reach region 157. This is illustrated in FIG. 9, which shows the ions in a stable trajectory midway through regions 153 and 157. In this manner, the ions are acted upon by a substantially static and homogenous electric field during the remaining portion of their flight through the flight tube 65. The equipotential field lines generated by the electric field in this second state of the flight tube 65 are shown in FIG. 9.

By forcing the ions into such a helical trajectory, very long flight lengths can be attained with a modestly sized device. For example, in the concentric electrode embodiment of FIGS. 4 through 10, flight lengths of about seven meters can be realized using a flight tube of about 100 mm in length and 20 mm in diameter. This represents an enormous savings in space compared to conventional time-of-flight instruments. Using this specific construction, the flight length is doubled for every doubling of the number of orbits about the axis 130.

The entry angle θ determines the number of orbits and ultimately the flight time through the tube. This relationship is expressed in the following equation:

$$tof = L/[v_a \sin \theta] = L/[(2zQV/m)^{1/2} \sin \theta] \quad \text{(Equation 2)}$$

where tof is flight time, L is the length of the flight tube, $v_a$ is velocity after acceleration, m is mass, z is the number of charges on the molecule, Q is the magnitude of the electric charge, V is the accelerating potential and θ is the ion input angle. As noted above, angle θ is relative to the x-axis in the x-z plane.

As can be seen from Equation 2, the time of flight is proportional to the flight tube length and inversely proportional to the input angle, θ. Long flight times may thus be achieved using very little space. This provides more accuracy in measuring different m/z of closely related species since the temporal separation between species of similar m/z increases with the length of the flight path. This construction also makes the length of the ion flight path independent of the diameter of the interstitial region between the electrodes of the flight tube 65. In larger diameter flight tubes 65, the ions circumnavigate axis 130 fewer times than in smaller diameter flight tubes but the actual distance traveled is the same.

In an alternative mode of operation of the flight tube 65, the ions may be initially introduced and an input angle of θ=0°. As such, the ions would be trapped in the substantially static electric field proximate the ion inlet 160 with a negligible velocity component along the linear axis 130. The ions may be held to circulate in this region until a predetermined criterion, such as the lapse of a predetermined time period, is met. Once this predetermined criterion is met, a velocity component along the linear axis 130 may be imparted to the ions so that they move along the linear axis while making the same multiple circumnavigating trips as their counterparts described above. This velocity component can be imparted through the use of a fourth electrode (not illustrated) that is disposed to generate an electric field in interstitial region 153 along the direction of the linear axis 130.

The operating parameters for the embodiment of a time-of-flight mass analyzer including the ion flight tube of FIGS. 4 through 10 can be determined based on known parameters of the instrument. One of the most significant of the operating parameters that must be determined is the magnitude of the voltage that is to be applied to the electrodes (of known dimensions based on the design of the system) to guide the ions into a stable trajectory within the interstitial region, or "gap", between the electrodes. To this end, several operating parameters are known quantities and several must be calculated. An example of the known parameters in such an analyzer, include:

Ion mass: m=1000 a.m.u. =$1.66 \times 10^{-27}$ kg/a.m.u=$1.66 \times 10^{-24}$ kg
Charge magnitude: Q=$1.6 \times 10^{-19}$ coulombs/charge
Number of charges: z=1
Ion kinetic energy: 23.2 electron volts (eV)
Ion entrance velocity: $v_a$=$2.115 \times 10^3$ meters/second after acceleration
Device dimensions: 100 mm length=0.1 meters
  18.5 mm outside diameter
  13.2 mm inside diameter
  15.2 mm diameter at center of gap
  2 mm gap between electrodes
  Radius of stable orbit=r=7.6 mm=$7.6 \times 10^{-3}$ meters
  (radius taken midway of the gap between the electrodes).

The unknown parameters include the acceleration needed to guide the ions into a stable helical trajectory between the electrodes and the electrode voltage needed to attain this acceleration.

First, the requisite acceleration needed to guide the ions into a stable helical trajectory is determined. To this end, position x of the ion within the gap at radius r along the x-axis is given by the following equation:

$$x = r \sin(\theta) \quad \text{(Equation 3)}$$

where θ is the angular position around the circumference of the gap. This angle may be expressed in radians as the angular velocity of the ion, ω, times the time after entry into the gap, t. So, $$x = r \sin(\omega t) \quad \text{(Equation 4)}$$

Likewise, the y position of the ion along the y-axis is given by the following equation:

$$y = r \cos(\omega t). \quad \text{(Equation 5)}$$

The velocity in the x and y directions may be found by taking the derivative of the expressions for the position. For the velocity in the x-direction, the expression is as follows:

$$v_x = [v_a/r][r \cos(\omega t)] = v_a \cos(\omega t) \quad \text{(Equation 6)}$$

where $v_a$ is the velocity of the ion after acceleration as it enters the device. Similarly, velocity in the y-direction is given by the following equation:

$$v_y = [-v_a/r][r \sin(\omega t)] = -v_a \sin(\omega t) \quad \text{(Equation 7)}$$

Taking the derivative of the expressions for x and y velocity gives the expression for acceleration in the x and y directions. The expression for acceleration in the x-direction is therefore:

$$a_x = [v/r][v(-\sin(\omega t))] = (-v_a^2/r)\sin(\omega t) \quad \text{(Equation 8)}$$

while the expression for acceleration in the y-direction:

$$a_y = [v/r][-v(\cos(\omega t))] = (-v_a^2/r)\cos(\omega t) \quad \text{(Equation 9)}$$

To find the expression for the composite acceleration $a_c$ (the accelerations in the x and y directions), the expressions for the individual accelerations must be summed as vectors in their respective directions. This may be derived as follows:

$$a_c^2 = a_x^2 + a_y^2 \text{ or} \quad \text{(Equation 10)}$$

$$a_c = (a_x^2 + a_y^2)^{1/2} = [((-v_a^2/r)\sin(\omega t))^2 + ((-v_a^2/r)\cos(\omega t))^2]^{1/2} \text{ or} \quad \text{(Equation 11)}$$

$$a_c = [(v_a^4/r^2)\sin^2(\omega t) + (v_a^4/r^2)\cos^2(\omega t)]^{1/2} \text{ or} \quad \text{(Equation 12)}$$

$$a_c = [(v_a^4/r^2)(\sin^2(\omega t) + \cos^2(\omega t))]^{1/2} \quad \text{(Equation 13)}$$

Given that ($\sin^2(\omega t) + \cos^2(\omega t)$) is unity, the foregoing expression of Equation 13 simplifies to the following $$a_c = (v_a^4/r^2)^{1/2} \quad \text{(Equation 14)}$$

or $$a_c = v_a^2/r \quad \text{(Equation 15)}$$

Equation 15 is thus used to find the acceleration needed to direct the ions into a stable trajectory within the flight tube 65. To find the electric field strength E necessary to attain the acceleration calculated in Equation 15, it is possible to start with the following general force equation:

$$F = ma \quad \text{(Equation 16)}$$

In terms of electrical forces, Equation 16 translates to the following equation:

$$QE = ma \quad \text{(Equation 17)}$$

or $$E = ma/Q \quad \text{(Equation 18)}$$

where E is the electric field in volts/meter. Substituting the values for mass, acceleration and charge identified in the exemplary known parameters set forth above, a solution for the electric field magnitude E can be found. Using the equation for acceleration of Equation 15 and substituting the exemplary parameters, the value for $a_c$ is calculated as follows:

$$a_c = v_a^2/r = (2.115 \times 10^3)^2/(7.6 \times 10^{-3}) = 4.473 \times 10^6/7.6 \times 10^{-3} = 5.886 \times 10^8 \quad \text{(Equation 19)}$$

With the value of $a_c$ now being known, the magnitude of the electric field E is reduced to the following value:

$$E = ma/Q = (1.66 \times 10^{-24})(5.886 \times 10^8)/(1.6 \times 10^{-19}) = (9.771 \times 10^{-16})/(1.6 \times 10^{-19}) = 6.107 \times 10^3 \text{ volts/meter} = 6.107 \text{ volts/millimeter} \quad \text{(Equation 20)}$$

Given that the gap between the electrodes in this example is 2 mm, the required electrode voltage, $V_e$, to get the desired field strength magnitude E is calculated in the following manner:

$$V_e = (2 \text{ mm})(6.107 \text{ volts/mm}) = 12.214 \text{ volts} \quad \text{(Equation 21)}$$

Several interesting observations may be made in connection with the foregoing equations. For example, it is apparent that the acceleration needed to force the ions into a stable trajectory is inversely proportional to the radius of the ring. If the gap between the electrodes is constant, increasing the ring diameter decreases the required acceleration and, therefore, the voltage required on the electrodes. For example, if the radius of the ring is doubled to 15.2 mm, the following parameters are obtained:

$$a_c = v_a^2/r = (2.115 \times 10^3)^2/(1.52 \times 10^{-2}) = (4.473 \times 10^6)/(1.52 \times 10^{-2}) = 2.943 \times 10^8 \quad \text{(Equation 22)}$$

That is, the acceleration is halved for every doubling of the radius. Likewise, the electric field will be halved and also the voltage required for establishing the required field. So, in a ring twice the radius of the original example, an ion of m/z 1000 with 23.2 eV kinetic energy will attain a stable trajectory with an electrode voltage of 6.107 volts.

Figure 11:
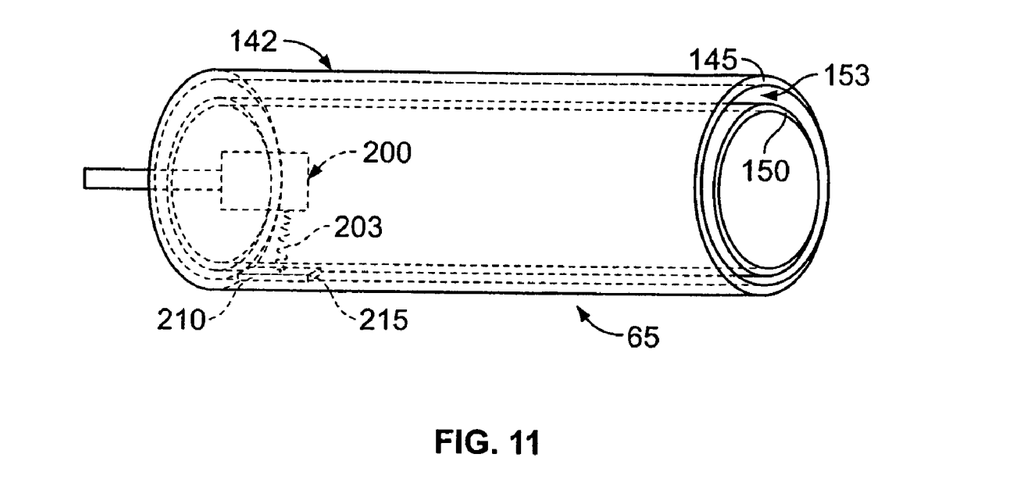
FIGS. 11 and 12 show the construction and operation of a further embodiment of a flight tube suitable for use in the time-of-flight mass spectrometer shown in FIG. 2.
Figure 12:
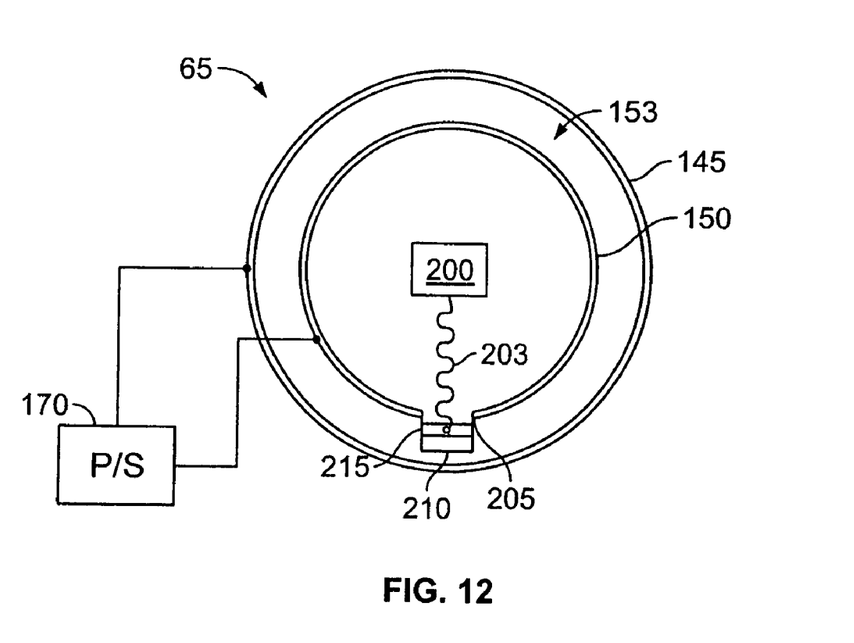

FIGS. 11 and 12 illustrate a further embodiment of a flight tube 65 suitable for use in the time-of-flight mass spectrometer of FIG. 2. In this embodiment, the ionizer/ion injector 60 is integrated with the flight tube 65. To this end, the ionization of a sample takes place within an inlet section 142 of the flight tube 65. Consequently, ions can proceed directly into the electric field of the interstitial region 153 between electrodes 145 and 150 without first passing through a field-free region.

Various ionization techniques may be integrated with the flight tube 65. In the embodiment of FIGS. 11 and 12, a MALDI technique is employed. In this example, a laser generator, shown generally at 200, is disposed to direct a laser beam 203 through an opening 205 of inner electrode 150 to ionize an analyte that has been introduced into the flight tube 65 on a sample plate 210. Ions of the analyte that are ejected from the sample plate 210 then preferably pass through an ion beam focusing apparatus, shown generally at 215. The focused ion beam provides the ions directly to the electric field of interstitial region 153 where the ions proceed through the flight tube 65 in the manner described above.

Although the components used to execute the MALDI ionization technique are shown in different areas of the flight tube 65, alternate arrangements are also possible. For example, the laser generator 200 and the sample plate 210 may both be disposed within interstitial region 153 proximate inlet portion 142. Given the teachings herein, the specific integration of the flight tube 65 and ionizer/ion injector 60 are principally based on design requirements.

Numerous modifications may be made to the foregoing system without departing from the basic teachings thereof. Although the present invention has been described in substantial detail with reference to one or more specific embodiments, those of skill in the art will recognize that changes may be made thereto without departing from the scope and spirit of the invention as set forth in the appended claims.

What is claimed is:

1. A time-of-flight mass analyzer comprising:
   an ionizer adapted to provide ions of a sample substance to be analyzed;
   a flight tube accepting ions provided from the ionizer, said flight tube adapted to constrain said ions to a substantially helical ion flight path using a generally static electric field, the flight tube comprising
   a first electrode having a generally cylindrical electrode surface facing an interior portion thereof, said first electrode further having an ion inlet disposed through a side thereof;
   a second electrode having a generally cylindrical electrode surface facing an exterior portion thereof, said second electrode being concentrically disposed with said first electrode, said second electrode further having an opening along an arcuate portion of the electrode surface in a region proximate said ion inlet;
   a third electrode having an arcuate electrode surface facing an exterior portion thereof, said third electrode being disposed in said arcuate opening of said second cylindrical electrode; and
   an ion detector disposed to detect ions exiting said flight tube;
   at least one timer adapted to determine the flight time of said ion along an ion path that comprises at least said substantially helical ion path.

2. A time-of-flight mass analyzer as claimed in claim 1 wherein said ionizer is integrated with said flight tube.

3. A time-of-flight mass analyzer as claimed in claim 1 wherein said substantially helical ion path is defined by a linear axis, said ions being provided to said flight tube with a velocity component in the direction of said linear axis.

4. A time-of-flight mass analyzer as claimed in claim 1 wherein said substantially helical ion path is defined by a linear axis, said ions being provided to said flight tube with a negligible velocity component in the direction of said linear axis whereby said ions initially remain circulating in a region proximate an input of said flight tube.

5. A time-of-flight mass analyzer as claimed in claim 4 and further comprising:
   an electrode disposed for use in generating an electric field that imparts a velocity component in a direction along said linear axis to said ions whereby said ions move away from said region proximate the input of said flight tube.

6. A time-of-flight mass analyzer as claimed in claim 1 wherein said flight tube comprises:
   an inlet portion having an ion inlet, said inlet portion being substantially free of electric fields;
   an ion deflection portion having a substantially static electric field, said ion deflection portion being adapted to direct ions received from said inlet portion along said substantially helical ion flight path.

7. A time-of-flight analyzer as claimed in claim 6 and further comprising:
   at least one power supply connected to said flight tube to generate a first generally static electric field in said ion deflection portion, said power supply further being alternately operable between at least a first state in which said inlet portion is substantially free of electric fields, and a second state in which a second generally static electric field is generated in said inlet portion.

8. A time-of-flight mass analyzer as claimed in claim 7 wherein said first and second generally static electric fields have substantially the same magnitude.

9. A time-or-flight mass analyzer as claimed in claim 1 and further comprising:
   at least one power supply connected to said first, second and third electrodes, said power supply being operable to generate a first generally static electric field between said first and second electrodes, said power supply further being alternately operable between at least a first state in which the region between said first and third electrodes proximate said ion inlet is generally field free, and a second state in which a second generally static electric field is generated in the region between said first electrode and said second and third electrodes.

10. A time-or-flight mass analyzer as claimed in claim 9 wherein said first and second generally static electric fields have substantially the same magnitude.

11. A time-or-flight mass analyzer as claimed in claim 9 wherein said ions are provided to said flight tube at a predetermined kinetic energy.

12. A time-or-flight mass analyzer as claimed in claim 11 wherein the magnitude of said first generally static electric field is selected based on said predetermined kinetic energy to guide said ions into a stable trajectory along said substantially helical ion flight path.

13. A time-of-flight mass analyzer as claimed in claim 12 wherein said first and second generally static electric fields have substantially the same magnitude.

14. A flight tube arrangement for use in a time-of-flight mass analyzer comprising:
  a first electrode having a generally cylindrical electrode surface facing an interior portion thereof, said first electrode further having an ion inlet disposed through a side thereof;
  a second electrode having a generally cylindrical electrode surface facing an exterior portion thereof, said second electrode being concentrically disposed with said first cylindrical electrode, said second electrode further having an opening through an arcuate portion of the electrode surface at least in a region proximate said ion inlet;
  a third electrode having an arcuate electrode surface facing an exterior portion thereof, said third electrode being disposed in said arcuate opening of said second electrode; and
  at least one power supply connected to said first, second and third electrodes, said power supply being operable to generate a generally static electric field between said first and second electrodes, said power supply further being alternately operable between at least a first state in which the region between said first and third electrodes proximate said ion inlet is generally field free, and a second state in which a generally static electric field is generated in the region between said first electrode and said second and third electrodes.

15. A flight tube for use in a time-of-flight mass analyzer comprising:
  a plurality of concentric electrodes disposed about a linear axis;
  where a first portion of the plurality of concentric electrodes form an inlet region-that is substantially free of electric fields; and
  where a second portion of the plurality of concentric electrodes form an ion deflection region having a substantially static electric field, where direct ions received from said inlet region into the ion deflection region are directed along a generally helical ion flight path defined by said substantially static electric field.

16. A time-of-flight mass analyzer comprising:
  an ionizer adapted to generate ions of a sample substance to be analyzed;
  a flight tube having at least one linear portion defined by a linear axis, said flight tube further having an input region accepting ions generated by the ionizer, said flight tube adapted to constrain said ions in a substantially static electric field having non-linear equipotential field lines that circumvent said linear axis;
  said ions being provided to said input region of said flight tube at an angle that is tangential to said equipotential field lines of said substantially static electric field to thereby initially trap said ions in said input region of said flight tube;
  an electrode disposed for use in generating an electric field that imparts a velocity component along said linear axis to said ions whereby said ions move away from said input region of said flight tube;
  an ion detector disposed to detect ions exiting said flight tube;
  at least one timer adapted to determine the flight time of said ions along an ion path that comprises at least said flight tube.

17. A time-of-flight mass analyzer as claimed in claim 16 wherein said ionizer is integrated with said flight tube.

18. A time-of-flight mass analyzer as claimed in claim 16 wherein said ions make multiple circumnavigating trips along a path defined by said non-linear equipotential field lines as said ions further travel in the direction of said linear axis.

19. A time-of-flight mass analyzer as claimed in claim 18 wherein said ions travel along a substantially helical ion flight path.

20. A time-of-flight mass analyzer comprising:
  an ionizer adapted to provide ions of a sample substance to be analyzed;
  a flight tube accepting ions provided from the ionizer, the flight tube comprising
    a first electrode having a generally cylindrical electrode surface having ail ion inlet disposed through a side thereof;
    a second electrode having a generally cylindrical electrode surface, said second electrode being concentrically disposed with said first electrode, said second electrode further having an opening along an arcuate portion of the electrode surface proximate said ion inlet of said first electrode;
    a third electrode having an arcuate electrode surface, said third electrode being disposed in said arcuate opening of said second cylindrical electrode;
  an ion detector disposed to detect ions exiting said flight tube; and
  at least one timer adapted to determine the flight time of said ion along an ion path that comprises at least said substantially helical ion path.

21. A time-of-flight mass analyzer as claimed in claim 20 and further comprising:
  at least one power supply connected to said first, second and third electrodes, said power supply being operable to generate a first generally static electric field between said first and second electrodes, said power supply further being alternately operable between at least a first state in which the region between said first and third electrodes proximate said ion inlet is generally field free, and a second state in which a second generally static electric field is generated in the region between said first electrode and said second and third electrodes.

22. A time-of-flight mass analyzer as claimed in claim 21 wherein said first and second generally static electric fields have substantially the same magnitude.

23. A time-of-flight mass analyzer as claimed in claim 21 wherein said ions are provided to said flight tube at a predetermined kinetic energy.

24. A time-of-flight mass analyzer as claimed in claim 23 wherein the magnitude of said first generally static electric field is selected based on said predetermined kinetic energy to guide said ions into a stable trajectory along said substantially helical ion flight path.

25. A time-of-flight mass analyzer as claimed in claim 24 wherein said first and second generally static electric fields have substantially the same magnitude.

26. A flight tube arrangement for use in a time-of-flight mass analyzer comprising:
   a first cylindrical electrode having an ion inlet disposed through a side thereof
   a second cylindrical electrode concentrically disposed with said first cylindrical electrode, said second cylindrical electrode further having an arcuate opening in a region proximate said ion inlet;
   a third arcuate disposed in said arcuate opening of said second electrode; and
   at least one power supply connected to said first cylindrical electrode, said second cylindrical electrode and said third arcuate electrode, said power supply being operable to generate a generally static electric field between said first and second cylindrical electrodes, said power supply further being alternately operable between at least a first state in which the region between said first cylindrical electrode and said third arcuate electrode proximate said ion inlet is generally field free, and a second state in which a generally static electric field is generated in the region between said first cylindrical electrode and said second cylindrical electrode and said third arcuate electrode.

* * * * *